United States Patent
Rowlands et al.

(10) Patent No.: US 12,012,636 B2
(45) Date of Patent: Jun. 18, 2024

(54) PULMONARY HYPERTENSION BIOMARKER

(71) Applicant: NOVARTIS AG, Basel (CH)

(72) Inventors: Marianna Rowlands, Cambridge, MA (US); Clemence Anne Jeanne Marie Tessier, Saint Louis (FR); Paul Andrew Whittaker, Cambridgeshire (GB)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 17/651,481

(22) Filed: Feb. 17, 2022

(65) Prior Publication Data

US 2022/0389507 A1 Dec. 8, 2022

Related U.S. Application Data

(63) Continuation of application No. 16/460,487, filed on Jul. 2, 2019, now abandoned, which is a continuation of application No. 15/315,908, filed as application No. PCT/IB2015/054082 on May 29, 2015, now abandoned.

(30) Foreign Application Priority Data

Jun. 3, 2014 (EP) .................... 14170962

(51) Int. Cl.
*C12Q 1/6883* (2018.01)
*G01N 33/68* (2006.01)

(52) U.S. Cl.
CPC ....... *C12Q 1/6883* (2013.01); *G01N 33/6863* (2013.01); *G01N 33/6884* (2013.01); *C12Q 2600/106* (2013.01); *C12Q 2600/158* (2013.01); *G01N 2333/521* (2013.01); *G01N 2800/12* (2013.01); *G01N 2800/321* (2013.01); *G01N 2800/52* (2013.01)

(58) Field of Classification Search
CPC .................................................. C12Q 1/6883
See application file for complete search history.

(56) References Cited

U.S. PATENT DOCUMENTS

| | | |
|---|---|---|
| 2006/0019272 A1 | 1/2006 | Geraci et al. |
| 2012/0295797 A1 | 11/2012 | Jones et al. |
| 2012/0328567 A1 | 12/2012 | Bushnell et al. |
| 2017/0088897 A1 | 3/2017 | Rowlands et al. |
| 2020/0002768 A1 | 1/2020 | Rowlands et al. |

FOREIGN PATENT DOCUMENTS

| | | |
|---|---|---|
| CN | 101318932 A | 12/2008 |
| JP | 2006230241 A | 9/2006 |
| KR | 101362951 B1 | 2/2014 |
| WO | 2009123730 A1 | 10/2009 |
| WO | 2011080050 A2 | 7/2011 |
| WO | 2013064810 A1 | 5/2013 |
| WO | 2015186037 A1 | 12/2015 |

OTHER PUBLICATIONS

Damas, Arterioscler Thromb Vase Biol. 2007; 27:614-620.
Dorfmüller et al., "Progress in pulmonary arterial hypertension pathology: relighting a torch inside the tunnel," Am J Respir Crit Care Med. Aug. 1, 2012;186(3):210-2.
Grant, American Journal of Pathology, vol. 160, No. 4, Apr. 2002.
International Search Report and Written Opinion for International Application No. PCT/IB2015/054082, dated Aug. 4, 2015 (12 pages).
Olschewski Respiration 2015;89:513-514.
Paulin et al., "G-protein-coupled receptors and pulmonary arterial hypertension (PAH)," Drug Discovery Today: Disease Models. Sep. 1, 2012; 9(3):e109-17.
Perras et al., "Pulmonary lymphoid neogenesis in idiopathic pulmonary arterial hypertension," Am J Respir Crit Care Med. Feb. 1, 2012;185(3):311-21.
Simonneau J Am Coll Cardiol 2009;54: S43-54 © 2009.
Soon et al., "Elevated levels of inflammatory cytokines predict survival in idiopathic and familial pulmonary arterial riypertension," Circulation. Aug. 31, 2010 ;122(9):920-7.

*Primary Examiner* — Nizal S Chandrakumar
(74) *Attorney, Agent, or Firm* — K&L Gates LLP

(57) ABSTRACT

Pulmonary hypertension is a progressive disease of various origins that is associated with vascular remodelling and results in right heart dysfunction. Accumulating evidence indicates important roles of immune cells and inflammatory chemokines in the pathogenesis and progression of pulmonary hypertension. We have identified CCL21 as anti-remodelling efficacy biomarker for pulmonary hypertension. CCL21 was found to be highly sensitive and specific in discriminating pulmonary hypertension patients from matched controls. CCL21 was upregulated in pulmonary hypertension and down-regulated with treatment with an anti-remodelling agent.

20 Claims, 6 Drawing Sheets

PULMONARY HYPERTENSION BIOMARKER

RELATED APPLICATIONS

This application is a continuation application of U.S. application Ser. No. 16/460,487 filed on Jul. 2, 2019, now abandoned, which is a continuation application of U.S. application Ser. No. 15/315,908 filed on Dec. 2, 2016, now abandoned, which is a national stage application, filed under 35 U.S.C. § 371, of International Application No. PCT/IB2015/054082, filed on May 29, 2015, which claims the benefit of and priority to EP Application No. 14170962.6 filed on Jun. 3, 2014, the entire contents of each of which are incorporated herein by reference in their entireties.

FIELD OF THE INVENTION

The invention is in the field of biomarkers in respiratory disease. In particular, it relates to the use of CCL21 expression as a biomarker for pulmonary hypertension.

Background of the Invention

Pulmonary hypertension is a progressive disease of various origins that is associated with a poor prognosis and results in right heart dysfunction. In all its variant presentations, this disease is estimated to affect up to 100 million people worldwide[1]. According to the current classification of pulmonary hypertension, which was agreed upon at the 4th World Symposium on Pulmonary Hypertension in 2008, five categories of chronic pulmonary hypertension exist.

Pulmonary hypertension (PH) is defined as a mean rise in pulmonary arterial pressure >25 mmHg at rest (>30 mmHg following exercise). Group 1 PH can be further subdivided into diseases where increased pulmonary vascular resistance is due to pre-capillary micro-angiopathy (diagnosed as a pre-capillary wedge pressure <15 mmHg). Within this group we find idiopathic pulmonary arterial hypertension (IPAH) and familial pulmonary arterial hypertension, associated pulmonary arterial hypertension, pulmonary arterial hypertension with venous/capillary involvement, & persistent pulmonary hypertension of the newborn. Group 2 includes pulmonary hypertension due to left heart diseases whereas Group 3 includes pulmonary hypertension associated with lung disease/hypoxemia (e.g. COPD) and Group 4 pulmonary hypertension associated with chronic thromboembolic disorders[2].

Despite advances in understanding of the underlying pathobiology of pulmonary hypertension and some improvements in diagnosis and development of novel therapeutics, there is still significant unmet medical need and unacceptable rates of morbidity and mortality across the spectrum of pulmonary hypertension.

The subcategories of pulmonary hypertension differ in their underlying causes. However, they all are characterized by excessive pulmonary vasoconstriction and abnormal vascular remodelling unique plexiform lesions. Endothelial dysfunction associated with inflammation and oxidative stress and vascular smooth muscle cell (SMC) proliferation are prominent features of pulmonary arterial hypertension[3-5]. These structural changes suggest a switch from a quiescent state to a proliferative, apoptosis-resistant cellular phenotype[6,7]. Vascular remodelling leads to a chronic elevation of pulmonary vascular resistance, right heart failure and death.

Several studies have also suggested a role for immune mechanisms in pulmonary arterial hypertension pathophysiology[8]. Inflammatory cells and intense chemokine production have been detected within remodeled pulmonary arteries, and vascular stromal cells have been shown to be sensitive to inflammatory stimuli[9]. In addition, elevated circulating cytokine levels have been measured in IPAH[10,11]. Up to one-third of patients with pulmonary arterial hypertension have circulating autoantibodies against various vascular self-antigens[12,13]. This suggests that the adaptive immune system, consisting of T and B lymphocytes, is involved, and indeed perivascular T and B lymphocytes have been detected in pulmonary vascular pulmonary arterial hypertension lesions[14]. Work on chronic inflammatory disorders and autoimmune diseases suggests that pathogenic antibodies and T cells may also be generated locally, in the targeted organ, in highly organized ectopic lymphoid follicles commonly called tertiary lymphoid tissues (tLTs)[15]. The role of tLTs in chronic pulmonary diseases is gaining in importance, especially in chronic obstructive pulmonary diseases[16], in idiopathic pulmonary fibrosis[17], and in obliterative bronchiolitis[18] and more recently pulmonary arterial hypertension[19]. Ectopic formation of secondary lymphoid tissue is initiated by the local attraction of naive T and B cells. Hence, the local production of homeostatic chemokines, and lymphocyte survival factors such as CCL21, attracting CCR7-expressing cells, such as mature DCs, naive T cells, and B cells[20], may be a critical event in the formation of ectopic lymphoid tissue. CCL21 expression, in particular, has been recently detected in tLTs in explanted lungs from patients with IPAH[19].

Current guidelines recommend the use of either brain natriuretic peptide (BNP) or the N-terminal fragment of pro-BNP (NT-proBNP) as biomarkers for mortality risk stratification. Natriuretic peptides were the first blood-derived markers of pulmonary hypertension. Nagaya et al were the first to show that plasma levels of BNP have a prognostic significance in pulmonary hypertension[21]. BNP levels predicted mortality in adult patients with symptomatic congenital heart disease[22], and BNP was also an independent predictor of therapy response. In a retrospective study in patients with pulmonary arterial hypertension, serial measurements of NT-proBNP (a by-product of BNP synthesis) were associated with survival[23]. Log-transformation of NT-proBNP values identified patients with pulmonary arterial hypertension who were at risk of adverse events with a specificity of 98% and a sensitivity of 60%[24].

However, BNP or NT-proBNP, are markers of myocardial strain, excessive stretching of the heart, and increased heart rate and do not directly reflect changes in distal pulmonary arteries in the lung, which are responsible for driving pulmonary hypertension pathophysiology. Remodelling changes in the heart and right ventricle specifically, are thought to follow pulmonary arteries remodelling. Thus, it is of crucial interest to assess and monitor pulmonary artery remodelling using surrogate non-invasive circulating biomarkers before the effect can be visualised in the right heart as a result of disease progression.

Biomarkers that specifically indicate the pathologic mechanism, the severity of the disease or the treatment response would be ideal tools for the management of pulmonary hypertension and would also facilitate the successful execution of future clinical trials.

SUMMARY OF THE INVENTION

It has now been found that CCL21 is a highly specific and sensitive biomarker for discriminating pulmonary hypertension patients from matched controls.

The invention therefore provides for a method for determining if a subject has pulmonary hypertension, comprising
a) providing a biological sample obtained from a subject suspected of having pulmonary hypertension;
b) assaying the biological sample for the level of CCL21 expression and/or CCL21 protein; and
c) comparing the amount of CCL21 expression and/or of CCL21 protein to a baseline value that is indicative of the amount of CCL21 expression and/or of CCL21 protein in a subject that does not have pulmonary hypertension;
wherein a statistical significant increased amount of CCL21 expression and/or of CCL21 protein compared to the baseline value is indicative of pulmonary hypertension.

The invention also provides for a method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension.

The invention also provides for a method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist.

In some embodiments of these aspects, the step of assaying comprises assaying the biological sample for a nucleic acid sequence of CCL21 expression, such as a nucleic acid is selected from CCL21 ribonucleic acid (RNA) or a fragment thereof and complementary deoxyribonucleic acid (cDNA) or a fragment thereof. In some other embodiments t step of assaying comprises assaying the biological sample for a CCL21 protein or fragment thereof.

In some other embodiments of these aspects the biological sample is selected from blood, serum, plasma, urine, saliva, faeces and a tissue sample.

In some other embodiments of these aspects the step of assaying comprises a technique selected from Northern blot analysis, polymerase chain reaction (PCR), reverse transcription-polymerase chain reaction (RT-PCR), TaqMan-based assays, direct sequencing, dynamic allele-specific hybridization, primer extension assays, oligonucleotide ligase assays, temperature gradient gel electrophoresis (TGGE), denaturing high performance liquid chromatography, high-resolution melting analysis, DNA mismatch-binding protein assays, capillary electrophoresis, Southern Blot, immunoassays, immunohistochemistry, ELISA, flow cytometry, Western blot, HPLC, and mass spectrometry.

The invention also provides a kit for use in determining if a subject has pulmonary hypertension predicting or for use in predicting the likelihood that a patient having pulmonary hypertension will respond to treatment with a pulmonary hypertension antagonist, the kit comprising,
a) at least one probe capable of detecting the presence of CCL21 expression and/or CCL21 protein; and
b) instruction for using the probe to assay a biological sample from the patient for the presence of CCL21 expression and/or CCL21 protein.

In some embodiments of this aspect, the probe is selected from an oligonucleotide that specifically hybridizes to a region of a nucleic acid sequence of CCL21 expression or binding molecule capable of binding a CCL21 protein or a fragment thereof.

In some embodiments of this aspect, the binding molecule is an antibody or a fragment thereof.

DETAILED DESCRIPTION OF THE INVENTION

Definitions

Figure 1B:
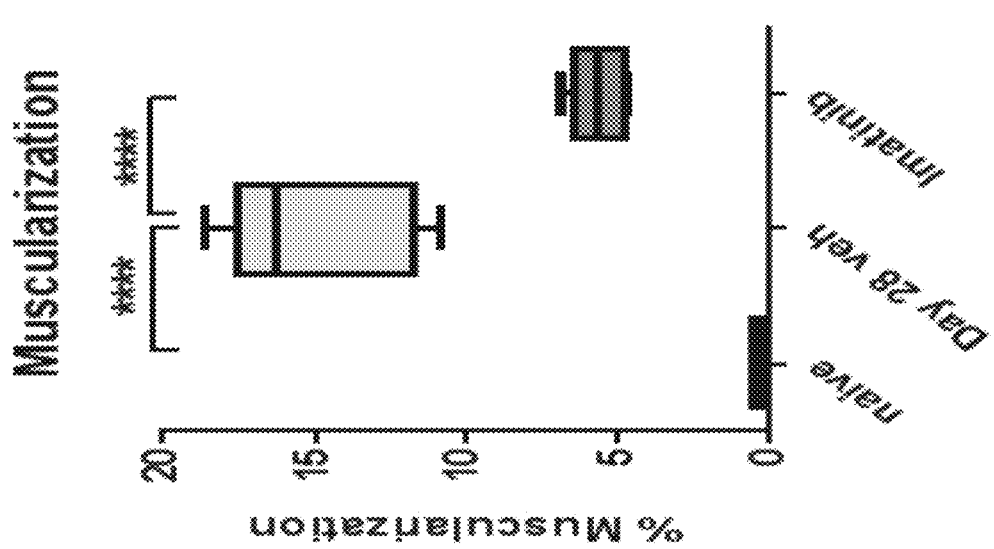
FIGS. 1A-1H: Candidate biomarker from lung mRNA expression profiles in the hypoxia/sugen rat model of PH following treatment with Imatinib.
Figure 1A:
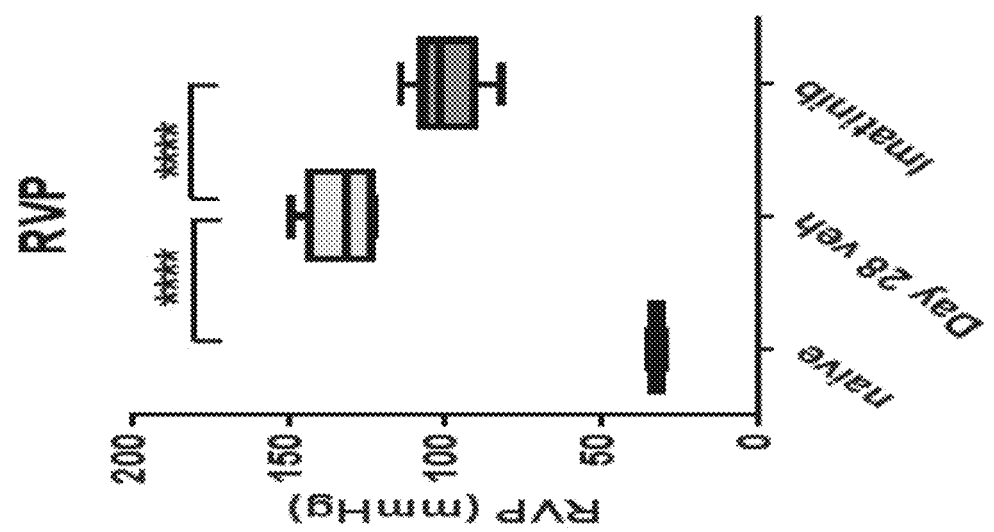
Figure 1D:
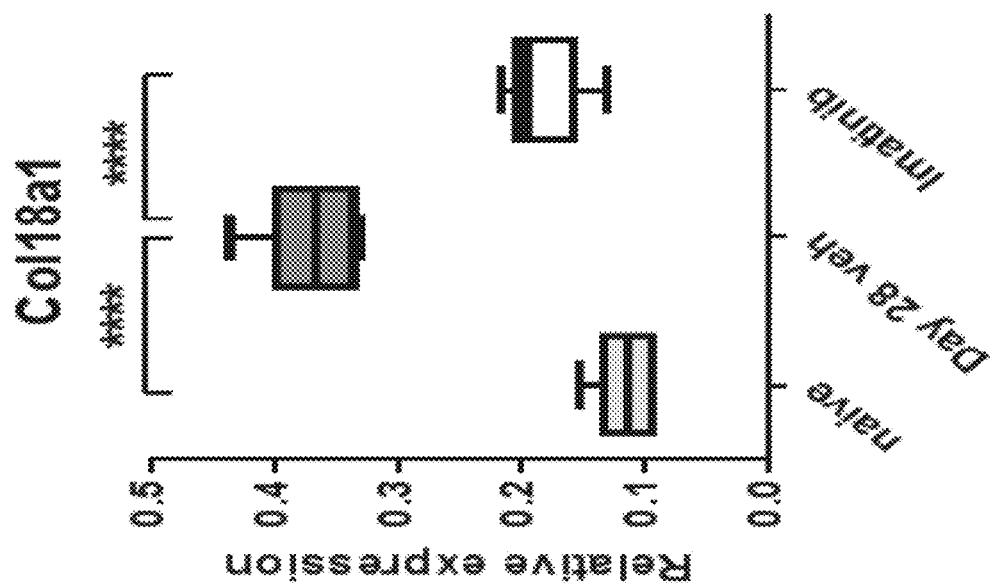
Figure 1C:
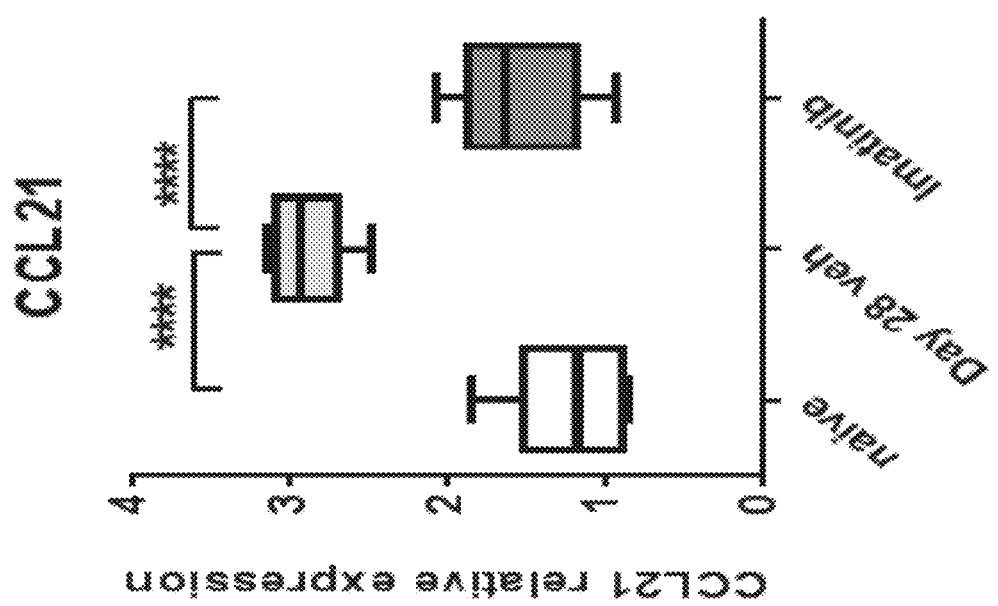
Figure 1F:
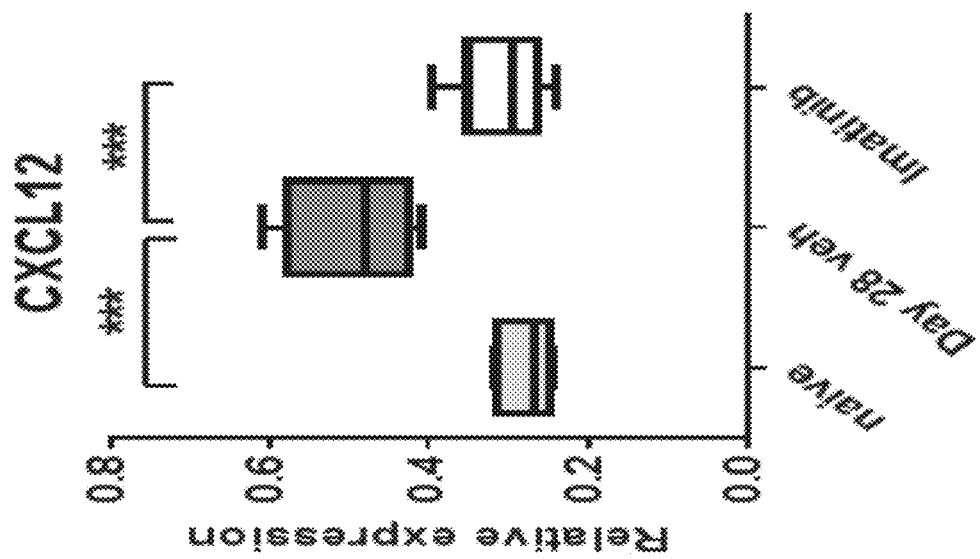
Figure 1E:
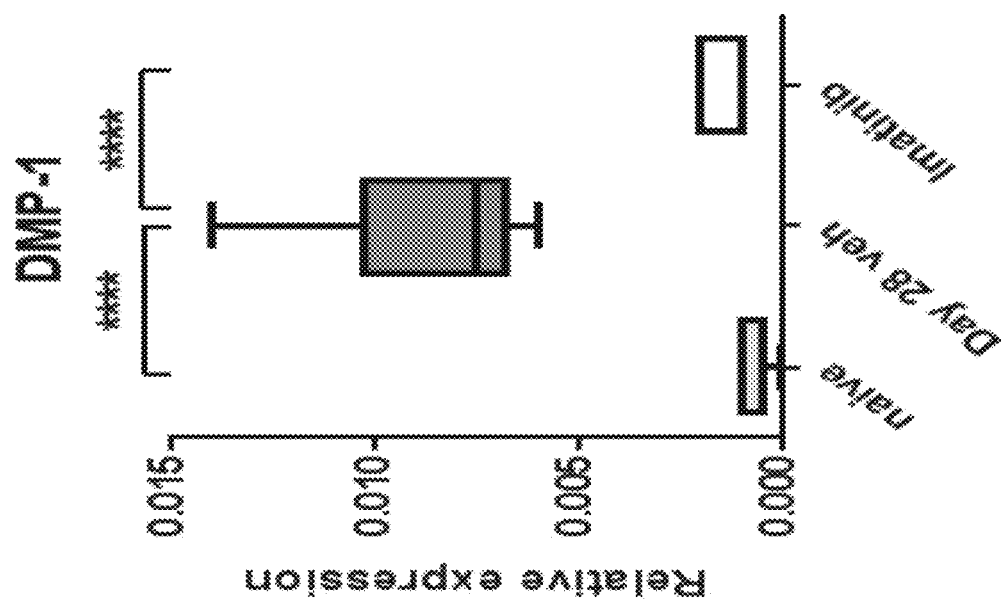
Figure 1H:
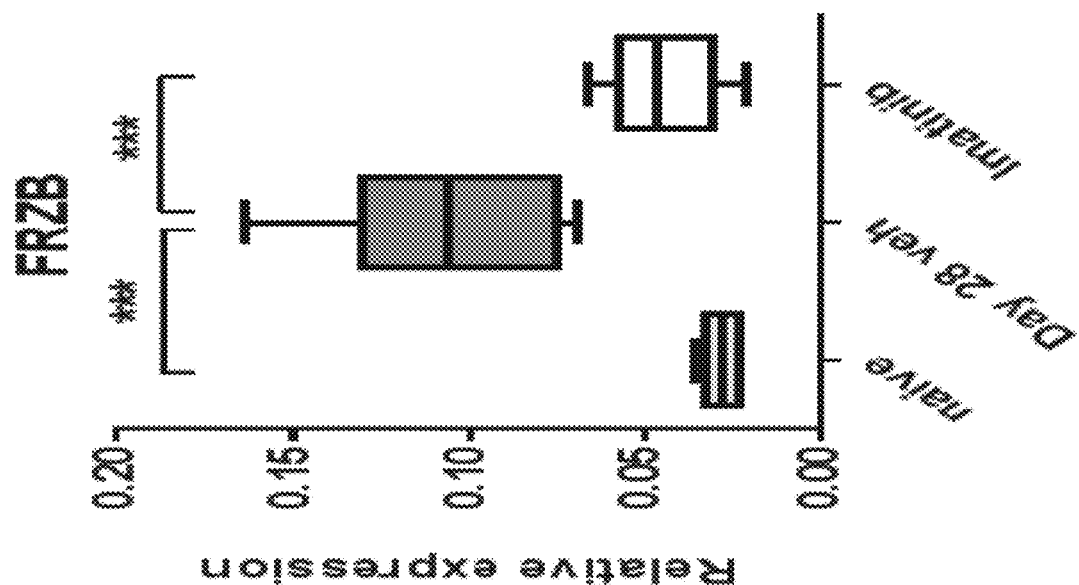
Figure 1G:
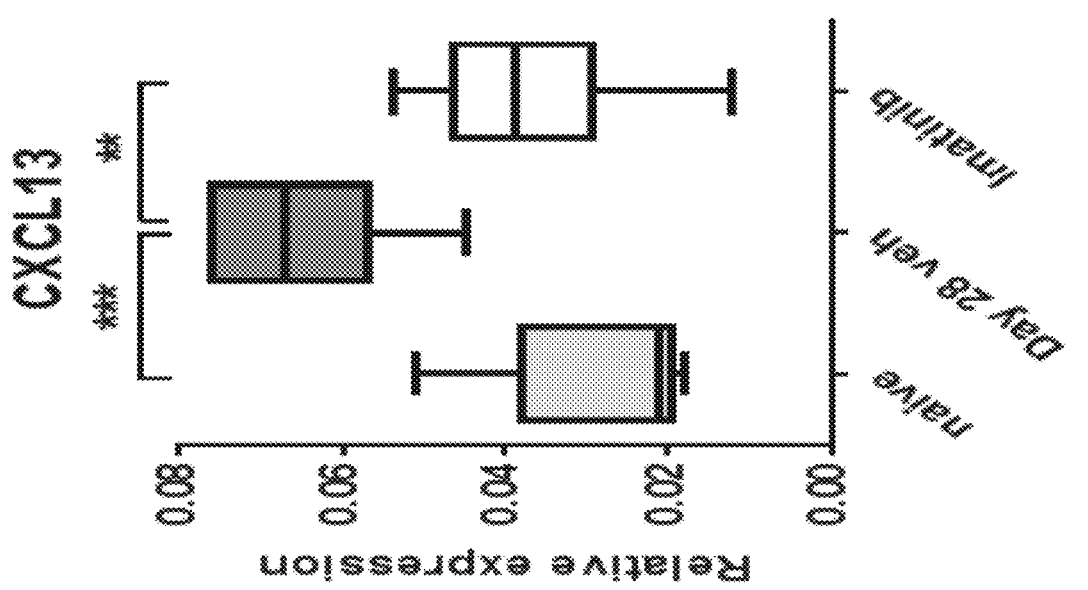

For purposes of interpreting this specification, the following definitions will apply and whenever appropriate, terms used in the singular will also include the plural and vice versa. Additional definitions are set forth throughout the detailed description.

The term "CCL21" refers to human CCL21, unless it is specified otherwise, having amino acid sequence for example as defined in ENST00000259607 (Ensembl).

The term "CCL21" refers to the human CCL21 gene, unless it is specified otherwise, having nucleotide sequence for example as defined in ENSP00000259607 (Ensembl).

The term "CCL21" is synonym to SCYA21; ECL; SLC; CKb9; TCA4; 6Ckine; 6Ckine; exodus-2; "chemokine (C—C motif) ligand 21 [*Homo sapiens* (human)]"; "C—C motif chemokine 21"; "beta chemokine exodus-2"; "Efficient Chemoattractant for Lymphocytes"; exodus-2; "secondary lymphoid tissue chemokine"; "small inducible cytokine subfamily A (Cys-Cys), member 21"

As used herein, the term "gene" means the gene and all currently known variants thereof.

As used herein, the term "level" refers to RNA and/or DNA and/or protein copy number of a biomarker according to the present invention. Typically, the level of a biomarker in a biological sample obtained from a patient under therapy is different (i.e. increased or decreased) from the level of the same biomarker in a similar sample obtained from a healthy subject.

The terms "assaying", "to assay", "detection", "detecting" and "to detect" refer to identifying the presence or absence of one or more biomarker(s). The terms "measurement", "measuring" and "to measure" refer to identify the presence, the absence or amount of one or more biomarker(s).

As used herein, a "baseline value" generally refers to the level (amount) of CCL21 expression (e.g. mRNA) or CCL21 polypeptide (or protein) in a comparable sample (e.g., from the same type of tissue as the tested tissue), from a "normal" healthy subject that does not exhibit pulmonary hypertension. If desired, a pool or population of the same tissues from normal subjects can be used, and the baseline value can be an average or mean of the measurements.

Suitable baseline values can be determined by those of skill in the art without undue experimentation. Suitable baseline values may be available in a database compiled from the values and/or may be determined based on published data or on retrospective studies of patients' tissues, and other information as would be apparent to a person of ordinary skill implementing a method of the invention. Suitable baseline values may be selected using statistical tools that provide an appropriate confidence interval so that measured levels that fall outside the standard value can be accepted as being aberrant from a diagnostic perspective, and predictive of pulmonary hypertension.

A "significant" increase in a value, as used herein, can refer to a difference which is reproducible or statistically significant, as determined using statistical methods that are appropriate and well-known in the art, generally with a probability value of less than five percent chance of the change being due to random variation. In general, a statistically significant value is at least two standard deviations from the value in a "normal" healthy control subject. Suitable statistical tests will be evident to a skilled worker. For example, a significant increase in the amount of a protein compared to a baseline value can be about 50%, 2-fold, or higher.

As used herein the terms "homolog" or "homologous" refers to a polynucleotide or polypeptide variant sharing common evolutionary ancestor or having at least 50% sequence identity with the wild type.

The term "binding molecule" as used herein means any protein or peptide that binds specifically to CCL21 polypeptide. "Binding molecule" includes, but it is not limited to, antibodies and fragments thereof, such as immunologically functional fragments. The term "immunologically functional fragment" of an antibody or immunoglobulin chain as used herein is a species of binding protein comprising a portion, regardless of how that portion is obtained or synthesized of an antibody (an antigen-binding portion) that lacks at least some of the amino acids present in a full-length chain but which is still capable of specifically binding CCL21.

The term "antibody" refers to an intact immunoglobulin or a functional fragment thereof. As used herein, the term "antibody" means a polypeptide comprising a framework region from an immunoglobulin gene or fragments thereof that specifically binds and recognizes an epitope, e.g. an epitope found on human CCL21. The term "antibody" includes whole antibodies (such as monoclonal, chimeric, humanised and human antibodies), including single-chain whole antibodies, and antigen-binding fragments thereof. The term "antibody" includes antigen-binding antibody fragments, single-chain antibodies, which can comprise the variable regions alone, or in combination, with all or part of the following polypeptide elements: hinge region, CH1, CH2, and CH3 domains of an antibody molecule.

As used herein, a binding molecule "capable of binding CCL21" is intended to refer to a binding molecule that binds to CCL21 with a $K_D$ of a $1\times10^{-6}$ M or less, or $1\times10^{-7}$ M or less, or $1\times10^{-8}$ M or less, or $1\times10^{-9}$ M or less, $1\times10^{-10}$ M or less.

As used herein, the term "subject" includes any human or non-human animal.

The term "non-human animal" includes all vertebrates, e.g., mammals and non-mammals, such as non-human primates, sheep, dogs, cats, horses, cows, chickens, amphibians, reptiles, etc.

The term "patient" includes any human or non-human animal.

The term "pulmonary hypertension antagonist" means any molecule which inhibits treat, prevent, cure pulmonary hypertension.

The term "treat", "treating", "treatment", "prevent", "preventing" or "prevention" includes therapeutic treatments, prophylactic treatments and applications in which one reduces the risk that a subject will develop a disorder or other risk factor. Treatment and/or prevention do not require the complete curing of a disorder and encompasses the reduction of the symptoms or underlying risk factors or at least a slowing down of the progression of the disease.

The term "comprising" means "including" as well as "consisting" e.g., a composition "comprising" X may consist exclusively of X or may include something additional e.g., X+Y.

The term "about" in relation to a numerical value x means, for example, x+10%. References to a percentage sequence identity between two amino acid sequences means that, when aligned, that percentage of amino acids are the same in comparing the two sequences. This alignment and the percent homology or sequence identity can be determined using software programs known in the art, for example those described in section 7.7.18 of Current Protocols in Molecular Biology (F. M. Ausubel et al., eds., 1987) Supplement 30. A preferred alignment is determined by the Smith-Waterman homology search algorithm using an affine gap search with a gap open penalty of 12 and a gap extension penalty of 2, BLOSUM matrix of 62. The Smith-Waterman homology search algorithm is disclosed in Smith & Waterman (1981) Adv. Appl. Math. 2: 482-489

CCL21 as Biomarker for Pulmonary Hypertension

Chemokine (C—C motif) ligand 21 (CCL21) is a small cytokine belonging to the CC chemokine family. CCL21 is one of several CC cytokine genes involved in immunoregulatory and inflammatory processes. The CC cytokines are proteins characterized by two adjacent cysteines. Similar to other chemokines the protein encoded by this gene inhibits haemopoiesis and stimulates chemotaxis. This protein is chemotactic in vitro for thymocytes and T cells and particularly naive T-cells., but not for B cells, macrophages, or neutrophils. It is a high affinity functional ligand for chemokine receptor 7 that is expressed on T and B lymphocytes[25]. CCL21 is thought to play a role in mediating homing of lymphocytes to secondary lymphoid organs. More recently, CCL21 expression has been detected in ectopic formation of secondary lymphoid tissue in tLTs in explanted lungs from patients with idiopathic pulmonary arterial hypertension[19]. In this study, CCL21 was studied in both human and rat samples. The rat and human CCL21 protein sequences are 67% identical which indicates a high degree of homology between the two species.

Methods of Diagnosis and Treatment

The present invention provides for a method for determining if a subject has pulmonary hypertension, comprising
  a) providing a biological sample obtained from a subject suspected of having pulmonary hypertension;
  b) assaying the biological sample for the level of CCL21 expression and/or CCL21 protein; and
  c) comparing the amount of CCL21 expression and/or of CCL21 protein to a baseline value that is indicative of the amount of CCL21 expression and/or of CCL21 protein in a subject that does not have pulmonary hypertension;
wherein a statistical significant increased amount of CCL21 expression and/or of CCL21 protein compared to the baseline value is indicative of pulmonary hypertension.

The present invention also provides for a method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist.

Furthermore, the present invention provides for a method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension.

In embodiments of the present invention, the step of assaying comprises assaying the biological sample for a nucleic acid of CCL21 expression The result of CCL21 gene expression may be a polynucleotide (or nucleic acid). A polynucleotide or nucleic acid is a molecule comprising a chain of at least two nucleic acid monomers which can be deoxyribonucleoside, ribonucleosides and any modified nucleoside thereof. Specifically included are DNA molecules as well as genomic and cDNA sequences, RNA molecules such as mRNA and unspliced or partly spliced transcripts and splicing products.

In one embodiment, the method for determining if a subject has pulmonary hypertension, the method comprises
a) providing a biological sample obtained from a subject suspected of having pulmonary hypertension;
b) assaying the biological sample for the level of CCL21 expression and/or CCL21 protein; and
c) comparing the amount of CCL21 expression and/or of CCL21 protein to a baseline value that is indicative of the amount of CCL21 expression and/or of CCL21 protein in a subject that does not have pulmonary hypertension; wherein a statistical significant increased amount of CCL21 expression and/or of CCL21 protein compared to the baseline value is indicative of pulmonary hypertension; wherein the step of assaying comprises assaying the biological sample for a nucleic acid sequence of CCL21 expression and wherein the nucleic acid is selected from ribonucleic acid (RNA) or a fragment thereof and complementary deoxyribonucleic acid (cDNA) or a fragment thereof. Preferably the nucleic acid is cDNA amplified from CCL21 mRNA.

In another embodiment, the method of predicting the likelihood that a patient having pulmonary arterial hypertension will respond to treatment with a pulmonary arterial hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist; wherein the step of assaying comprises assaying the biological sample for a nucleic acid sequence of CCL21 expression and wherein the nucleic acid is selected from ribonucleic acid (RNA) or a fragment thereof and complementary deoxyribonucleic acid (cDNA) or a fragment thereof. Preferably the nucleic acid is cDNA amplified from CCL21 mRNA.

In yet another embodiment, the method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; wherein the step of assaying comprises assaying the biological sample for a nucleic acid sequence of CCL21 expression and wherein the nucleic acid is selected from ribonucleic acid (RNA) or a fragment thereof and complementary deoxyribonucleic acid (cDNA) or a fragment thereof. Preferably the nucleic acid is cDNA amplified from CCL21 mRNA.

In other embodiments of the present invention, the step of assaying comprises assaying the biological sample for a CCL21 protein or fragment thereof.

CCL21 protein (or polypeptide) according to the present invention comprise the polypeptide obtained by (complete or incomplete) transcription and translation of the human CCL21 gene.

Polypeptide variants are also included in the present invention. A variant polypeptide includes a molecule containing one or more deletions, insertions and/or substitutions compared to the wild type polypeptides obtained by transcription and translation of the wild type human CCL21 gene or by translation of the wild type polyribonucleotide transcripts of that gene.

The biomarker according to the present invention may be a fragment or a degradation product of CCL21 polypeptide (or protein).

In one embodiment, the method for determining if a subject has pulmonary hypertension, the method comprises
a) providing a biological sample obtained from a subject suspected of having pulmonary hypertension;
b) assaying the biological sample for the level of CCL21 expression and/or CCL21 protein; and
c) comparing the amount of CCL21 expression and/or of CCL21 protein to a baseline value that is indicative of the amount of CCL21 expression and/or of CCL21 protein in a subject that does not have pulmonary hypertension; wherein a statistical significant increased amount of CCL21 expression and/or of CCL21 protein compared to the baseline value is indicative of pulmonary hypertension; and wherein the step of assaying comprises assaying the biological sample for a CCL21 protein or fragment thereof.

In another embodiment, the method for determining if a subject has pulmonary hypertension, the method comprises
a) providing a biological sample obtained from a subject suspected of having pulmonary hypertension;
b) assaying the biological sample for the level of CCL21 expression and/or CCL21 protein; and
c) comparing the amount of CCL21 expression and/or of CCL21 protein to a baseline value that is indicative of the amount of CCL21 expression and/or of CCL21 protein in a subject that does not have pulmonary hypertension; wherein a statistical significant increased amount of CCL21 expression and/or of CCL21 protein compared to the baseline value is indicative of pulmonary hypertension; wherein the step of assaying comprises assaying the biological sample for a CCL21 protein or fragment thereof; and wherein the pulmonary hypertension is idiopathic pulmonary arterial hypertension.

In another embodiment, the method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist; and wherein the step of assaying comprises assaying the biological sample for a CCL21 protein or fragment thereof.

In another embodiment, the method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist; wherein the step of assaying comprises assaying the biological sample for a CCL21 protein or fragment thereof; and wherein the pulmonary hypertension is idiopathic pulmonary arterial hypertension.

In yet another embodiment, the method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; and wherein the step of assaying comprises assaying the biological sample for a CCL21 protein or fragment thereof.

In another embodiment, the method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; and wherein the step of assaying comprises assaying the biological sample for a CCL21 protein or fragment thereof; and wherein the pulmonary hypertension is idiopathic pulmonary arterial hypertension.

In other embodiments of the present invention, the step of assaying comprises assaying the biological sample for a modified nucleic acid sequence of CCL21 expression or for a modified CCL21 protein or fragment thereof.

Modifications of polynucleotides or polypeptides are well-known in the art. The modifications may be performed on one or more nucleosides or amino acid residues of the polynucleotides or polypeptides, respectively. Alternatively, or in combination with the afore-mentioned chemical modifications, the link between monomers may be modified. Further known modifications include the conjugation of tags or labels to the polynucleotide or polypeptide biomarker.

Chemical modifications of polynucleotides, include, but are not limited to, replacement of hydrogen by an alkyl, acyl or amino group, alteration of sugar moieties or inter-sugar linkages (i.e. phosphorothioate), labeling of nucleotides with radio-nucleotides (i.e. $^{32}P$), conjugation with tags or labeling molecules such as fluorescent tags (i.e. rhodamine, fluorescein, Cy3 and/or Cy5, chemiluminescent tags, chromogenic tags or other labels (i.e. digoxigenin or biotin and magnetic particles). Modification of the sugar moieties, purine and pyrimidine heterocycles as well as heterocyclic analogues and tautomers thereof are also included herein. Illustrative examples are diaminopurine 8-oxo-$N^6$-methyladenine, 7-deazaxanthine, 7-deazaguanine, $N^4,N^4$-ethanocytosin, $N^6,N^6$-ethano-2,6-diaminopurine, 5-methylcytosine, 5-($C^3$-$C^6$)-alkynylcytosine, 5-fluorouracil, 5bromouracil, 2-hydroxy-5methyl-4-triazolopyridin, isocytosin, isoguanin, inosine and the examples described in U.S. Pat. No. 5,432,272; Scheit, Nucleotide Analogs, John Wiley, New York, 1980; Freier and Altmann, Nucl. Acid Res., 1997, 25(22), 4429-43; Toulme', J. J., Nature Biotechnology 19:17-18 (2001); Manoharan M.; Biochemica et Biophysica Acta 1489:117-139 (1999); Freier S. M., Nucleic acid Research, 25:4429-4443 (1997); Uhlman E., Drug Discovery & Development, 3: 203-213 (2000); Herdewin P., Antisense & Nucleic acid Drug Dev., 10:297-310 (2000).

A wide variety of labeling and conjugation techniques are known by those skilled in the art. Polynucleotides or nucleic acids labeling can be achieved for example by oligo-labeling, nick translation, end-labeling or PCR amplification using a labeled primer.

The chemical modifications of a polynucleotide biomarker according to the present invention preferably comprise radioisotope labeling and/or fluorescent agent labeling. More preferably, the polynucleotide biomarker(s) according to the present invention, especially when amplified in number copies by polymerase chain reaction (PCR), comprises a fluorescent tag (e.g. TaqMan® Gene Expression Assays consist of a pair of unlabeled PCR primers and a TaqMan® probe with a FAM™ or VIC® dye label on the 5' end, and minor groove binder (MGB) nonfluorescent quencher (NFQ) on the 3' end.

Biological Samples

In embodiments of the present invention, the biological sample is selected from blood, serum, plasma, urine, saliva, feces and a tissue sample.

A sample which is "provided" can be obtained by the person (or machine) conducting the assay, or it can have been obtained by another, and transferred to the person (or machine) carrying out the assay.

Many suitable sample types will be evident to a skilled worker. In one embodiment of the invention, the sample is a blood sample, such as whole blood, plasma, or serum (plasma from which clotting factors have been removed). For example, peripheral or venous plasma or serum can be used. In another embodiment, the sample is urine, sweat, or another body fluid into which proteins are sometimes removed from the blood stream. In the case of urine, for example, the protein is likely to be broken down, so diagnostic fragments of the proteins of the invention can be screened for. In another embodiment, the sample is pulmonary tissue, which is harvested, e.g., after a biopsys. Methods for obtaining samples and preparing them for analysis are conventional and well-known in the art.

In one embodiment, the method for determining if a subject has pulmonary hypertension, the method comprises
  a) providing a biological sample obtained from a subject suspected of having pulmonary hypertension;
  b) assaying the biological sample for the level of CCL21 expression and/or CCL21 protein; and
  c) comparing the amount of CCL21 expression and/or of CCL21 protein to a baseline value that is indicative of the amount of CCL21 expression and/or of CCL21 protein in a subject that does not have pulmonary hypertension;
  wherein a statistical significant increased amount of CCL21 expression and/or of CCL21 protein compared to the baseline value is indicative of pulmonary hypertension; wherein the step of assaying comprises assaying the biological sample for a nucleic acid sequence of CCL21 expression; wherein the nucleic acid is selected from ribonucleic acid (RNA) or a fragment thereof and complementary deoxyribonucleic acid (cDNA) or a fragment thereof; and wherein the biological sample is selected from blood or plasma or serum. Preferably the nucleic acid is cDNA amplified from CCL21 mRNA.

In another embodiment, the method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist; wherein the step of assaying comprises assaying the biological sample for a nucleic acid sequence of CCL21 expression; wherein the nucleic acid is selected from ribonucleic acid (RNA) or a fragment thereof and complementary deoxyribonucleic acid (cDNA) or a fragment thereof and wherein the biological sample is selected from blood or plasma or serum. Preferably the nucleic acid is cDNA amplified from CCL21 mRNA.

In yet another embodiment, the method of treating a patient having pulmonary hypertension, comprising
  a) assaying a biological sample obtained from the patient for the level of CCL21 expression and/or CCL21 protein; and
  b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; wherein the step of assaying comprises assaying the biological sample for a nucleic acid sequence of CCL21 expression; wherein the nucleic acid is selected from ribonucleic acid (RNA) or a fragment thereof and CCL21 ribonucleic acid (RNA) complementary deoxyribonucleic acid (cDNA) or a fragment thereof and wherein the biological sample is selected from blood or plasma or serum. Preferably the nucleic acid is cDNA amplified from CCL21 mRNA.

In another embodiment, the method for determining if a subject has pulmonary hypertension, the method comprises
  a) providing a biological sample obtained from a subject suspected of having pulmonary hypertension;
  b) assaying the biological sample for the level of CCL21 expression and/or CCL21 protein; and
  c) comparing the amount of CCL21 expression and/or of CCL21 protein to a baseline value that is indicative of the amount of CCL21 expression and/or of CCL21 protein in a subject that does not have pulmonary hypertension; wherein a statistical significant increased amount of CCL21 expression and/or of CCL21 protein compared to the baseline value is indicative of pulmonary hypertension; wherein the step of assaying comprises assaying the biological sample for a CCL21 protein or fragment thereof and wherein the biological sample is selected from blood or plasma or serum.

In another embodiment, the method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist; wherein the step of assaying comprises assaying the biological sample for a CCL21 protein or fragment thereof and wherein the biological sample is selected from blood or plasma or serum.

In yet another embodiment, the method of treating a patient having pulmonary hypertension, comprising
  a) assaying a biological sample obtained from the patient for the level of CCL21 expression and/or CCL21 protein; and
  b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; wherein the step of assaying comprises assaying the biological sample for a CCL21 protein or fragment thereof and wherein the biological sample is selected from blood or plasma or serum.

In some embodiments, there is provided a method of treating a patient having pulmonary hypertension, comprising
  a) assaying a biological sample obtained from the patient for the level of CCL21 expression and/or CCL21 protein; and
  b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension and wherein the pulmonary hypertension antagonist is selected from Calcium channel blockers, Phosphodiesterase (PDE) 5 inhibitors, guanylate cyclase (sGC) stimulator, Endothelin receptor antagonists (ERAs) and Prostacyclin agonists.

Detection (or Assaying) Methods

A variety of methods known or apparent to those skilled in the art maybe employed to carry out gene or protein expression profiling.

In some embodiments the step of assaying comprises a technique selected from Northern blot analysis, polymerase chain reaction (PCR), reverse transcription-polymerase chain reaction (RT-PCR), TaqMan-based assays, direct sequencing, dynamic allele-specific hybridization, primer extension assays, oligonucleotide ligase assays, temperature gradient gel electrophoresis (TGGE), denaturing high performance liquid chromatography, high-resolution melting analysis, DNA mismatch-binding protein assays, capillary electrophoresis, Southern Blot, immunoassays, immunohistochemistry, ELISA, flow cytometry, Western blot, HPLC, and mass spectrometry.

In general, methods of gene expression profiling can be divided into two large groups: methods based on hybridization analysis of polynucleotides, and other methods based on biochemical detection or sequencing of polynucleotides. The most commonly used methods known in the art for the quantification of mRNA expression in a sample include northern blotting and in situ hybridization (Parker & Barnes, Methods in Molecular Biology 106:247-283 (1999)); RNAse protection assays (Hod, Biotechniques 13:852-854 (1992)); and reverse transcription polymerase chain reaction (RT-PCR) (Weis et al., Trends in Genetics 8:263-264 (1992)).

Alternatively, antibodies may be employed that can recognize specific duplexes, including DNA duplexes, RNA duplexes, and DNA-RNA hybrid duplexes or DNA-protein duplexes. Various methods for determining expression of mRNA or protein include, but are not limited to, gene expression profiling, polymerase chain reaction (PCR) including quantitative real time PCR (qRT-PCR), microarray analysis that can be performed by commercially available equipment, following manufacturer's protocols, such as by using the Affymetrix GenChip technology, serial analysis of gene expression (SAGE) (Velculescu et al., Science 270:484-487 (1995); and Velculescu et al., Cell 88:243-51 (1997)), MassARRAY, Gene Expression Analysis by Massively Parallel Signature Sequencing (MPSS) (Brenner et al., Nature Biotechnology 18:630-634 (2000)), proteomics, immunohistochemistry (IHC), etc. Preferably mRNA is quantified. Such mRNA analysis is preferably performed using the technique of polymerase chain reaction (PCR), or by microarray analysis. Where PCR is employed, a preferred form of PCR is quantitative real time PCR (qRT-PCR).

Immunohistochemistry methods are also suitable for detecting the expression levels of the biomarker of the present invention. Thus, antibodies or antisera, preferably polyclonal antisera, and most preferably monoclonal antibodies specific for each marker are used to detect expression. The antibodies can be detected by direct labeling of the antibodies themselves, for example, with radioactive labels, fluorescent labels, hapten labels such as, biotin, or an enzyme such as horse radish peroxidase or alkaline phosphatase. Alternatively, unlabeled primary antibody is used in conjunction with a labeled secondary antibody, comprising antisera, polyclonal antisera or a monoclonal antibody specific for the primary antibody. Immunohistochemistry protocols and kits are well known in the art and are commercially available.

Expression levels can also be determined at the protein level, for example, using various types of immunoassays or proteomics techniques.

In immunoassays, the target diagnostic protein marker is detected by using an antibody specifically binding to the markers. The antibody typically will be labeled with a detectable moiety. Numerous labels are available which can be generally grouped into the following categories: Radioisotopes, such as 35S, 14C, 125I, 3H, and 131I. The antibody can be labeled with the radioisotope using the techniques described in Current Protocols in Immunology, Volumes 1 and 2, Coligen et al. (1991) Ed. Wiley-Interscience, New York, New York, Pubs for example and radioactivity can be measured using scintillation counting.

Fluorescent labels such as rare earth chelates (europium chelates) or fluorescein and its derivatives, rhodamine and its derivatives, dansyl, Lissamine, phycoerythrin and Texas Red are available. The fluorescent labels can be conjugated to the antibody using the techniques disclosed in "Current Protocols in Immunology", supra, for example. Fluorescence can be quantified using a fluorimeter.

Various enzyme-substrate labels are available and U.S. Pat. No. 4,275,149 provides a review of some of these. The enzyme generally catalyzes a chemical alteration of the chromogenic substrate which can be measured using various techniques. For example, the enzyme may catalyze a color change in a substrate, which can be measured spectrophotometrically. Alternatively, the enzyme may alter the fluorescence or chemiluminescence of the substrate. Techniques for quantifying a change in fluorescence are described above. The chemiluminescent substrate becomes electronically excited by a chemical reaction and may then emit light which can be measured (using a chemiluminometer, for example) or donates energy to a fluorescent acceptor. Examples of enzymatic labels include luciferases (e.g., firefly luciferase and bacterial luciferase; U.S. Pat. No. 4,737,456), luciferin, 2,3-dihydrophthalazinediones, malate dehydrogenase, urease, peroxidase such as horseradish peroxidase (HRPO), alkaline phosphatase, β-galactosidase, glucoamylase, lysozyme, saccharide oxidases (e.g., glucose oxidase, galactose oxidase, and glucose-6-phosphate dehydrogenase), heterocyclic oxidases (such as uricase and xanthine oxidase), lactoperoxidase, microperoxidase, and the like. Techniques for conjugating enzymes to antibodies are described in O'Sullivan et al. (1981) Methods for the Preparation of Enzyme-Antibody Conjugates for use in Enzyme Immunoassay, in Methods in Enzym. (ed J. Langone & H. Van Vunakis), Academic press, New York 73: 147-166.

Examples of enzyme-substrate combinations include, for example: horseradish peroxidase (HRPO) with hydrogen peroxidase as a substrate, wherein the hydrogen peroxidase oxidizes a dye precursor (e.g., orthophenylene diamine (OPD) or 3,3',5,5'-tetramethyl benzidine hydrochloride (TMB)); alkaline phosphatase (AP) with para-Nitrophenyl phosphate as chromogenic substrate; and β-D-galactosidase (β-D-Gal) with a chromogenic substrate (e.g., p-nitrophenyl-β-D-galactosidase) or fluorogenic substrate 4-methyl-umbelliferyl-β-D-galactosidase.

Numerous other enzyme-substrate combinations are available to those skilled in the art. For a general review of these, see U.S. Pat. Nos. 4,275,149 and 4,318,980.

In other versions of immunoassay techniques, the antibody need not be labeled, and the presence thereof can be detected using a labeled antibody which binds to the antibody. For the detection of human CCL21 protein in plasma and serum samples a custom made immunoassay on the Mesoscale Discovery® (MSD) platform was used. MSD's electrochemiluminescence detection technology uses SULFO-TAG™ labels, which emit light upon electrochemical stimulation initiated at the electrode surfaces of MULTI-ARRAY and MULTI-SPOT® microplates.

Thus, the diagnostic immunoassays herein may be in any assay format, including, for example, competitive binding assays, direct and indirect sandwich assays such ELISA, and immunoprecipitation assays.

In one embodiment, the method for determining if a subject has pulmonary hypertension, the method comprises
a) providing a biological sample obtained from a subject suspected of having pulmonary hypertension;
b) assaying the biological sample for the level of CCL21 expression and/or CCL21 protein; and
c) comparing the amount of CCL21 expression and/or of CCL21 protein to a baseline value that is indicative of the amount of CCL21 expression and/or of CCL21 protein in a subject that does not have pulmonary hypertension; wherein a statistical significant increased amount of CCL21 expression and/or of CCL21 protein compared to the baseline value is indicative of pulmonary hypertension; wherein the step of assaying comprises assaying the biological sample for a nucleic acid sequence of CCL21 expression by PCR or RT-PCR; wherein the nucleic acid is selected from ribonucleic acid (RNA) or a fragment thereof and complementary deoxyribonucleic acid (cDNA) or a fragment thereof; and wherein the biological sample is selected from blood or plasma or serum. Preferably the nucleic acid is cDNA amplified from CCL21 mRNA.

In another embodiment, the method of predicting the likelihood that a patient having pulmonary hypertension will respond to treatment with a pulmonary hypertension antagonist, comprising, assaying a biological sample obtained from the patient for the level of CCL21 expression and/or CCL21 protein; and wherein an increased level of CCL21 expression and/or CCL21 protein relative to a baseline value is indicative of an increased likelihood that the patient will respond to treatment with the pulmonary hypertension antagonist; wherein the step of assaying comprises assaying the biological sample for a nucleic acid sequence of CCL21 expression by PCR or RT-PCR; wherein the nucleic acid is selected from ribonucleic acid (RNA) or a fragment thereof and complementary deoxyribonucleic acid (cDNA) or a fragment thereof; and wherein the biological sample is selected from blood or plasma or serum. Preferably the nucleic acid is cDNA amplified from CCL21 mRNA.

In yet another embodiment, the method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; wherein the step of assaying comprises assaying the biological sample for a nucleic acid sequence of CCL21 expression by PCR or RT-PCR; wherein the nucleic acid is selected from ribonucleic acid (RNA) or a fragment thereof and complementary deoxyribonucleic acid (cDNA) or a fragment thereof; and wherein the biological sample is selected from blood or plasma or serum. Preferably the nucleic acid is cDNA amplified from CCL21 mRNA.

In another embodiment, the method for determining if a subject has pulmonary hypertension, the method comprises
a) providing a biological sample obtained from a subject suspected of having pulmonary hypertension;
b) assaying the biological sample for the level of CCL21 expression and/or CCL21 protein; and
c) comparing the amount of CCL21 expression and/or of CCL21 protein to a baseline value that is indicative of the amount of CCL21 expression and/or of CCL21 protein in a subject that does not have pulmonary hypertension; wherein a statistical significant increased amount of CCL21 expression and/or of CCL21 protein compared to the baseline value is indicative of pulmonary hypertension; wherein the step of assaying comprises assaying the biological sample for a CCL21 protein or fragment thereof by immunoassays or ELISA and wherein the biological sample is selected from blood or plasma or serum.

In another embodiment, the method of predicting the likelihood that a patient having pulmonary hypertension will respond to treatment with a pulmonary hypertension antagonist, comprising, assaying a biological sample obtained from the patient for the level of CCL21 expression and/or CCL21 protein by immunoassays or ELISA; and wherein an increased level of CCL21 expression and/or CCL21 protein relative to a baseline value is indicative of an increased likelihood that the patient will respond to treatment with the pulmonary hypertension antagonist; wherein the step of assaying comprises assaying the biological sample for a CCL21 protein or fragment thereof and wherein the biological sample is selected from blood or plasma or serum.

In yet another embodiment, the method of treating a patient having pulmonary hypertension, comprising
a) assaying a biological sample obtained from the patient for the level of CCL21 expression and/or CCL21 protein; and
b) administering a therapeutically effective amount of a pulmonary hypertension antagonist if the patient has a statistical significant increased amount of CCL21 expression and/or CCL21 protein compared to the amount of CCL21 expression and/or of CCL21 protein to a baseline value that is indicative of the amount of CCL21 expression and/or of CCL21 protein in a subject that does not have pulmonary hypertension; wherein the step of assaying comprises assaying the biological sample for a CCL21 protein or fragment thereof by immunoassays or ELISA and wherein the biological sample is selected from blood or plasma or serum.

Kits of the Invention

The invention provides for a kit for use in determining if a subject has pulmonary hypertension predicting or for use in predicting the likelihood that a patient having pulmonary hypertension will respond to treatment with a pulmonary hypertension antagonist the kit comprising,
a) at least one probe capable of detecting the presence of CCL21 expression and/or CCL21 protein; and
b) instruction for using the probe to assay a biological sample from the patient for the presence of CCL21 expression and/or CCL21 protein.

In one embodiment, the probe is selected from an oligonucleotide that specifically hybridizes to a region of a nucleic acid sequence of CCL21 expression such as gene-specific or gene-selective probes and/or primers, for quantitating the expression of CCL21.

The kit may optionally further comprise reagents for the extraction of RNA from samples, in particular fixed paraffin-embedded tissue samples and/or reagents for RNA amplification. The kit may comprise containers (including microtiter plates suitable for use in an automated implementation of the method), each with one or more of the various reagents (typically in concentrated form), for example, prefabricated microarrays, buffers, the appropriate nucleotide triphosphates (e.g., dATP, dCTP, dGTP and dTTP; or rATP, rCTP, rGTP and UTP), reverse transcriptase, DNA polymerase, RNA polymerase.

In another embodiment, the probe is a binding molecule capable of binding a CCL21 protein or a fragment thereof. Preferably, the binding molecule is an antibody or a fragment thereof.

Other binding molecules may be molecules having a scaffold based on fibronectin type III domain (e.g., the tenth module of the fibronectin type III (10 Fn3 domain)), adnectin (Adnectins®), molecules comprising ankyrin derived repeat modules, Affibody® molecules, Anticalins® molecules, Affilin® molecules and protein epitope mimetics.

EXAMPLES

This invention is further illustrated by the following examples which should not be construed as limiting.

1. Hypoxia/Sugen Rat Model Genechip Profiling

The rat Hypoxia/Sugen model of PH was used to carry out a comparative transcriptome profiling between rat lung samples with experimental PH and naïve rat lungs.

All animal procedures were conducted in accordance with the British Home Office regulations (Scientific Procedures) Act of 1986, UK.

Sugen (250 mg; SU5416; Sigma-Aldrich®) was dissolved in vehicle (12.5 ml; 0.5% (wt/vol) carboxyl methylcellulose sodium, 0.9% (wt/vol) NaCl, 0.4% (vol/vol) polysorbate, 0.9% (vol/vol) benzyl alcohol in deionized water), sonicated for 15 min and then vortexed. On day 0, animals were anaesthetized, weighed and received Sugen 20 mg/kg by sub-cutaneous injection. Animals were placed in the hypoxia chamber and the O2 level was slowly decreased to 10%. Control animals remained in room air (21% O2) to serve as normoxic controls for the study. After 2 weeks, all animals were removed from the hypoxia chamber. At week 4, the animals were subjected to echocardiographic measurements under sevoflurane anaesthesia and monitored closely until fully recovered. Animals underwent RV catheterization for measurement of right ventricular pressure (RVP) under a mixture of ketamin and medetomidine anaesthesia. Following euthanasia by Schedule 1, the left lobe of the lung was removed, inflated and fixed in 10% formalin and embedded in paraffin for histological analysis. Lobes of the right lung were snap frozen for transcriptional profiling.

Frozen rat lung samples, collected in TT2 tissue bags (K Bioscience® Cat #520021) were crushed using the Covaris CryoPrep CP02. Total RNA from the crushed lung samples was extracted by RNeasy Mini kit according to the manufacturer's protocol (Qiagen™). Genomic DNA was removed by treatment with DNase I (Turbo DNase kit, Invitrogen). The exact quantification of RNA was determined with a NanoDrop ND-1000 spectrophotometer. RNA quality was assessed by analyzing 18S and 28S rRNAs by microfluidics-based electrophoresis on a 2100 Bioanalyzer (Agilent Technologies, Santa Clara, Calif.).

For microarray preparation and analysis, the Affymetrix One-Round In Vitro Transcription RNA Amplification Kit was used to amplify 1 μg of total RNA. The complementary DNA (cDNA) was synthesised with a primer containing oligo (dT) and T7 RNA polymerase promoter sequences. Double-stranded cDNA was then purified and used as a template to generate biotinylated cRNA. The quantity and quality of the amplified cRNA was assessed using a NanoDrop ND-1000 Spectrophotometer (Thermo Scientific) and an Agilent Bioanalyzer. The biotinylated cRNA was fragmented and hybridised to Affymetrix Rat GeneChip arrays 230_2. After hybridisation, the GeneChip arrays were washed, stained and scanned using a GeneChip Scanner 3000 7G. Affymetrix GeneChip Operating Software was used for image acquisition. Analysis was performed using GeneSpring GX 11.5.1 software (Agilent Technologies Inc., USA). Data normalisation was achieved using the Robust Multichip Analysis (RMA) algorithm and baseline transformation to the median of all samples.

Differentially expressed genes (>1.5 fold, p≤value 0.05, T-test) that encode for secreted proteins (likely to be detected in blood samples) and that are associated with remodeling processes were shortlisted for further validation (Table 1). Genes associated with remodelling were collated from the following sources: MetaCore pathway database (http://thomsonreuters.com/metacore formerly GeneGO), Ingenuity Pathway Analysis database (IPA) (http://www.ingenuity.com/products/ipa), Gene Prospector tool in Gene Navigator (http://hugenavigator.net/HuGENavigator). Genes annotated as secreted or detected in blood were found using the following sources: Ingenuity Pathway Analysis database (IPA) (http://www.ingenuity.com/products/ipa) and a proprietary data set (SECTRANS).

TABLE 1

Differentially expressed genes in lung samples of Hypoxia Sugen treated animals compared to naïve controls

| | Rat Gene Symbol | Rat Gene Title | Rat Entrez Gene ID | Fold change |
|---|---|---|---|---|
| 1 | Cyp1b1 | cytochrome P450, family 1, subfamily b, polypeptide 1 | 25426 | 46.4 |
| 2 | Grem1 | gremlin 1, cysteine knot superfamily, homolog (Xenopus laevis) | 50566 | 8.4 |
| 3 | Chia | chitinase, acidic | 113901 | 4.2 |
| 4 | Ccl2 | chemokine (C-C motif) ligand 2 | 24770 | 3.4 |
| 5 | Serpine1 | serine (or cysteine) peptidase inhibitor, clade E, member 1 | 24617 | 3.2 |
| 6 | Spp1 | secreted phosphoprotein 1 | 25353 | 3.1 |
| 7 | Il1r2 | interleukin 1 receptor, type II | 117022 | 3.1 |
| 8 | Frzb | frizzled-related protein | 295691 | 3.0 |

TABLE 1-continued

Differentially expressed genes in lung samples of Hypoxia Sugen treated animals compared to naive controls

|    | Rat Gene Symbol | Rat Gene Title | Rat Entrez Gene ID | Fold change |
|----|-----------------|----------------|--------------------|-------------|
| 9  | Il6 | interleukin 6 | 24498 | 2.9 |
| 10 | Cxcl13 | chemokine (C-X-C motif) ligand 13 | 498335 | 2.7 |
| 11 | Esm1 | endothelial cell-specific molecule 1 | 64536 | 2.7 |
| 12 | Mmrn1 | multimerin 1 | 500152 | 2.6 |
| 13 | Ccl21 | chemokine (C-C motif) ligand 21 | 298006 | 2.6 |
| 14 | Cthrc1 | collagen triple helix repeat containing 1 | 282836 | 2.6 |
| 15 | Plaur | plasminogen activator, urokinase receptor | 50692 | 2.5 |
| 16 | Tfpi2 | tissue factor pathway inhibitor 2 | 286926 | 2.4 |
| 17 | C6 | complement component 6 | 24237 | 2.3 |
| 18 | Dmp1 | dentin matrix acidic phosphoprotein 1 | 25312 | 2.3 |
| 19 | Ptgs2 | prostaglandin-endoperoxide synthase 2 | 29527 | 2.3 |
| 20 | Arhgap1 | Rho GTPase activating protein 1 | 311193 | 2.3 |
| 21 | LOC100363145 | stabilin 1 | 100363145 | 2.2 |
| 22 | Aqp1 | aquaporin 1 | 25240 | 2.2 |
| 23 | Fst | follistatin | 24373 | 2.1 |
| 24 | Reln | reelin | 24718 | 2.1 |
| 25 | Acp5 | acid phosphatase 5, tartrate resistant | 25732 | 2.1 |
| 26 | Col18a1 | collagen, type XVIII, alpha 1 | 85251 | 2.1 |
| 27 | Lpar6 | lysophosphatidic acid receptor 6 | 691774 | 2.0 |
| 28 | Nos3 | nitric oxide synthase 3, endothelial cell | 24600 | 2.0 |
| 29 | Cxcr4 | chemokine (C-X-C motif) receptor 4 | 60628 | 1.9 |
| 30 | Chi3l1 | chitinase 3-like 1 | 89824 | 1.9 |
| 31 | Adamts4 | ADAM metallopeptidase with thrombospondin type 1 motif, 4 | 66015 | 1.8 |
| 32 | Gdf15 | growth differentiation factor 15 | 29455 | 1.8 |
| 33 | Tac1 | tachykinin 1 | 24806 | 1.8 |
| 34 | Col1a1 | collagen, type I, alpha 1 | 29393 | 1.8 |
| 35 | Angpt2 | angiopoietin 2 | 89805 | 1.8 |
| 36 | Olr1 | oxidized low density lipoprotein (lectin-like) receptor 1 | 140914 | 1.8 |
| 37 | Timp1 | TIMP metallopeptidase inhibitor 1 | 116510 | 1.8 |
| 38 | Serpine2 | serine (or cysteine) peptidase inhibitor, clade E, member 2 | 29366 | 1.8 |
| 39 | Eln | elastin | 25043 | 1.8 |
| 40 | Vcan | versican | 114122 | 1.7 |
| 41 | Adora2b | adenosine A2B receptor | 29316 | 1.7 |
| 42 | Cxcl10 | chemokine (C-X-C motif) ligand 10 | 245920 | 1.7 |
| 43 | Gstp1 | glutathione S-transferase pi 1 | 24426 | 1.6 |
| 44 | Mmp14 | matrix metallopeptidase 14 (membrane-inserted) | 81707 | 1.6 |
| 45 | Hmox1 | heme oxygenase (decycling) 1 | 24451 | 1.6 |
| 46 | Ctsk | cathepsin K | 29175 | 1.6 |
| 47 | Il1r1 | interleukin 1 receptor, type I | 25663 | 1.6 |
| 48 | Pthlh | parathyroid hormone-like hormone | 24695 | 1.6 |
| 49 | Axl | Axl receptor tyrosine kinase | 308444 | 1.6 |
| 50 | Gch1 | GTP cyclohydrolase 1 | 29244 | 1.6 |
| 51 | Inhba | inhibin beta-A | 29200 | 1.5 |
| 52 | Cxcl12 | chemokine (C-X-C motif) ligand 12 (stromal cell-derived factor 1) | 24772 | 1.5 |
| 53 | Hp | haptoglobin | 24464 | 1.5 |
| 54 | Fn1 | fibronectin 1 | 25661 | 1.5 |
| 55 | Il6st | interleukin 6 signal transducer | 25205 | 1.5 |
| 56 | Il1rn | interleukin 1 receptor antagonist | 60582 | 1.5 |
| 57 | Des | desmin | 64362 | 1.5 |
| 58 | Vegfa | vascular endothelial growth factor A | 83785 | −1.5 |
| 59 | Ace | angiotensin I converting enzyme (peptidyl-dipeptidase A) 1 | 24310 | −1.6 |

2. Assessment of Candidate Biomarker mRNA Levels in the Hypoxia Sugen Rat Model of Idiopathic Pulmonary Arterial Hypertension Following Treatment with Imatinib All animal procedures were conducted as described above.

In this study, following administration of an initial dose of Sugen on day 0 and a period of 14 days in a hypoxia chamber following, rats were administered 100 mg/kg of Imatinib or vehicle control daily for a further two weeks.

Following euthanasia by Schedule 1, the left lobe of the lung was removed, inflated and fixed in 10% formalin and embedded in paraffin for histological analysis, by airway inflation. Tissue sections (3 μm) were stained with antibodies against von Willebrand factor (vWF) and α-smooth muscle actin (α-SMA). Slides were examined using a DMLB and confocal microscope, digital camera, and IM50 imaging software (Leica Microsystems, London, UK). Small pulmonary vessels (10-100 μm diameter indicated by vWF staining) were assessed for degrees of circumferential α-SMA-positive staining indicative of muscularisation. Lobes of the right lung were snap frozen for candidate biomarker mRNA expression measurements. Total RNA was extracted and underwent quality control as mentioned in section above.

cDNA was synthesised using the High Capacity RNA-to-cDNA Kit (Invitrogen) according to the kit manufacturer's protocol. QPCR was performed on an ABI Prism 7900HT sequence detection system (Applied Biosystems, USA), using TaqMan Universal PCR Master Mix (Applied Biosystems). Taqman assays were purchased from Applied Biosystems®. Relative expression was normalised to a combination of 10 different housekeeping genes. Data were analyzed using the SDS RQ Manager, software (Applied Biosystems, version 2.4). Normalised gene expression values for each gene ($2^{-\Delta ct}$) were plotted and analysed using a two-way ANOVA in GraphPad Prism 6.02.

The expression of all transcripts listed on Table 1 was assessed in lung samples from animals treated with vehicle or Imatinib. The following 6 gene transcripts were found to be upregulated in rat Hy/Su lungs and down-regulated with treatment with Imatinib: Ccl21, Col18a1, Cxcl12, Cxcl13, Dmp1, Frzb (FIGS. 1C-1H). In addition, we measured CCL21 mRNA expression levels in lung samples from groups treated with imatinib or vehicle on day 28 and control naïve animals and observed an increase of CCL21 mRNA levels in lungs of vehicle treated animals compared to naïve controls and a decrease following treatment with Imatinib. CCL21 expression levels in lung samples from these groups correlated significantly with both right ventricular pressure and arterial muscularisation ($P<0.0001$)

We therefore concluded that transcript levels of the above genes are down-regulated in response to an anti-remodelling agent in the lungs of animals with pulmonary hypertension as a result of the therapeutic drug administration.

3. Assessment of Candidate Biomarker mRNA Correlation with Vascular Remodelling Readouts in a Rat Hypoxia/Sugen Longitudinal All animal procedures were conducted as described above. In this study following administration of an initial dose of Sugen on day 0 and a period of 21 days in a hypoxia chamber, rats developed elevated right ventricular pressure and arterial muscularisation. Following euthanasia by Schedule 1, the left lobe of the lung was removed for histological analysis and the right lobe for mRNA analysis. We measured all 6 candidate biomarker mRNA expression levels in lung samples from the following study timepoints: weeks 3, 5, 8 and 14 and naïve animals (n=6 in each group). Pearson correlation was used to assess the significance of the correlation between candidate biomarker mRNA expression and percentage of muscularisation, right ventricular pressure (RVP) and number of occluded vessels. Transcript expression of all markers assessed in lung samples from these groups correlated significantly with at least two of the three vascular remodeling readouts: percentage of arterial muscularisation, percentage of occluded vessel and right ventricular pressure (Table 2). We therefore concluded that transcripts of the candidate biomarker assessed are indicative of the degree of vascular remodeling.

TABLE 2

Correlations of candidate biomarker transcript expression levels with vascular remodeling readouts

| Transcript | R value muscularisation | P value muscularisation |
|---|---|---|
| CCL21 | 0.7102 | <0.0001 |
| Cxcl12 | 0.626 | <0.0001 |
| Frzb | 0.6292 | <0.0001 |
| Cxcl13 | 0.6164 | <0.0001 |
| Col18a1 | 0.4072 | 0.0152 |
| Dmp1 | 0.3933 | 0.0194 |

| Transcript | R value lumen occlusion | P value lumen occlusion |
|---|---|---|
| CCL21 | 0.7344 | <0.0001 |
| Cxcl12 | 0.5331 | 0.0008 |
| Frzb | 0.4921 | 0.0023 |
| Cxcl13 | 0.3482 | 0.0374 |
| Col18a1 | 0.347 | 0.0381 |
| Dmp1 | 0.1549 | 0.3671 |

| Transcript | R value RVP | R value RVP |
|---|---|---|
| CCL21 | 0.7164 | <0.0001 |
| Cxcl12 | 0.6611 | <0.0001 |
| Frzb | 0.7078 | <0.0001 |
| Cxcl13 | 0.7183 | <0.0001 |
| Col18a1 | 0.4877 | 0.0091 |
| Dmp1 | 0.4796 | 0.0031 |

4. Assessment of Candidate Biomarker Protein Levels in Serum and Plasma Samples of PH Patients and Matched Controls To determine whether circulating protein levels of candidate biomarkers are elevated in serum and plasma PH patient samples compare to matched controls, we developed immunoassays for CCL21, CXCL12, CXCL13 and Col181a and measured circulating levels of these in 30 PH patients and 25 age, ethnicity and gender ratio matched controls.

Human peripheral blood samples were obtained and handled in accordance with an approved Ethical Review Board application. Matched serum and plasma samples from 30 pulmonary hypertension patients were collected. Out of the 30 PH patients, 24.8% belonged to Group 1, 28.4% to Group 2, 10% to Groups 2 and 3, 33.3% to Group 3 and 3.5% to Group 4 according to the World Health Organisation (WHO) classification system (Dana Point 2008)[2]

Immunoassays using MSD Coated Custom plates were carried out as per manufacturer's recommendations. Briefly, plates were incubated with proprietary Diluent 2 at 25 μl/well, sealed with adhesive cover film and incubated for 30 minutes at room temperature on a plate shaker (300-1000 rpm). CCL21 Recombinant protein (R&D Systems®, cat #DY366, Part 841709) was reconstituted 1% BSA (Gibco, cat #15260-037)/PBS (Gibco, cat #14190) and was added at 10,000 pg/ml and 1:5 serial dilutions were performed with Diluent 2, with the $8^{th}$ point as the zero standard (0 pg/ml).

Standards, samples, and assay controls were added at 25 μl/well to MSD plate with Diluent 2. Plate was sealed and incubated at room temperature for 2 hours on a plate shaker (300-1000 rpm). The wells were then washed three times with wash buffer (0.05% Tween-20 in PBS pH7.4 Sigma™, cat #P3563-10PAK).

CCL21 detection and capture antibodies (Human CCL21/6Ckine DuoSet ELISA development system, R&D Systems®, cat #DY366, Parts 841707 and 841708, supplied with MSD Coated Custom Plate) were reconstituted according to the R&D System® DuoSet protocol, at a final concentration of 1 µg/ml. Detection antibody solution was added to the washed plate. The plate was sealed and incubated for 2 hours with shaking at room temperature. After a final wash step reverse pipetting was used to add 150 µl of 2× Read Buffer T (diluted with an equal volume of $H_2O$) and the plate was read using an MSD instrument SECTOR Imager 6000.

For the statistical analysis, an unpaired-t test was performed using GraphPad prism 6. A Receiver Operating Characteristic (ROC) curve analysis was performed using GraphPad Prism 6. The area under the curve (AUC), as generated by the software, reflects the specificity and the selectivity of the biomarker. An AUC of 1 indicates a biomarker 100% sensitive and specific in discriminating two populations.

Figure 2:
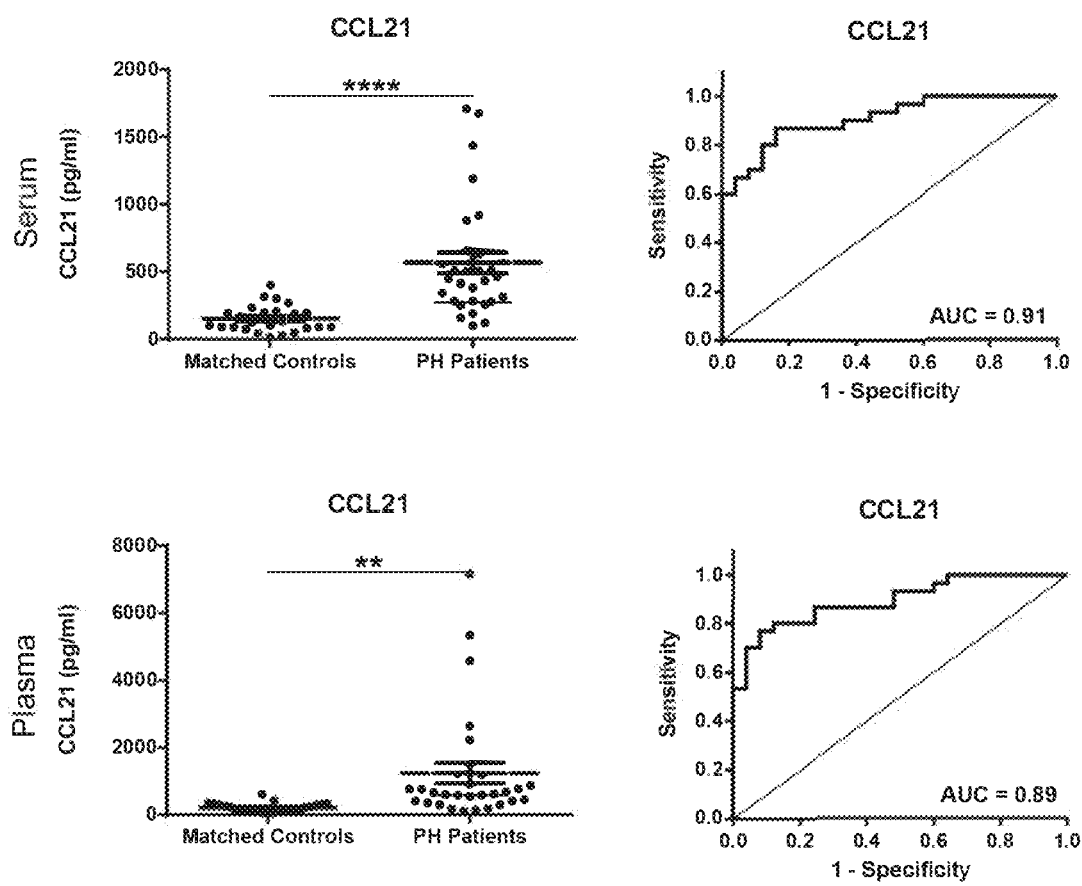
FIG. 2: Human CCL21 protein levels in serum and plasma samples from PH patients and matched controls (age, ethnicity, gender ratio-matched).

We found that CCL21, but not Col18a1, CXCL12 or 13 (data not shown), was up-regulated in PH patients compared to matched controls in both serum and plasma samples (FIG. 2). Receiver Operating Characteristics (ROC) curve analysis of the data sets indicated that CCL21 circulating levels are able to discriminate patients from controls with high sensitivity and specificity, with an are under the curve (AUC) of 0.91 in serum samples and 0.89 in plasma samples (FIG. 2). We therefore concluded that CCL21 is upregulated in serum and plasma samples of PH patients compared to matched controls and is able to discriminate patients from controls with high sensitivity/specificity 5. Human IHC CCL21 Protein Data from PH Patients Formalin fixed paraffin embedded tissue sections from PH were sourced from the University of Cambridge from patients undergoing lung transplantation under an approved informed consent and institutional agreement.

CCL21 was detected by immunohistochemistry on a Ventana Discovery XT using the following protocol. Briefly, sections were dewaxed using EZprep solution, and high pH8 antigen retrieval was performed using the Ventana cc1 reagent. CCL21 was detected using goat anti-human CCL21 antibody (R&D System® AF366, 3.33 ug/ml)—the antibody was incubated for 12 hours at room temperature. Secondary antibody was biotinylated rabbit anti-goat (DAKO E0466) diluted to 1/200, 20 minute incubation at 37° C. Biotinylated secondary antibody was detected using the DABMap kit. (Ventana 650-010). Sections were counterstained using Harris' haematoxylin and coverslipped. Images were scanned using the Aperio XT slide scanner and analysed using Definiens Tissue Studio.

Figure 3:
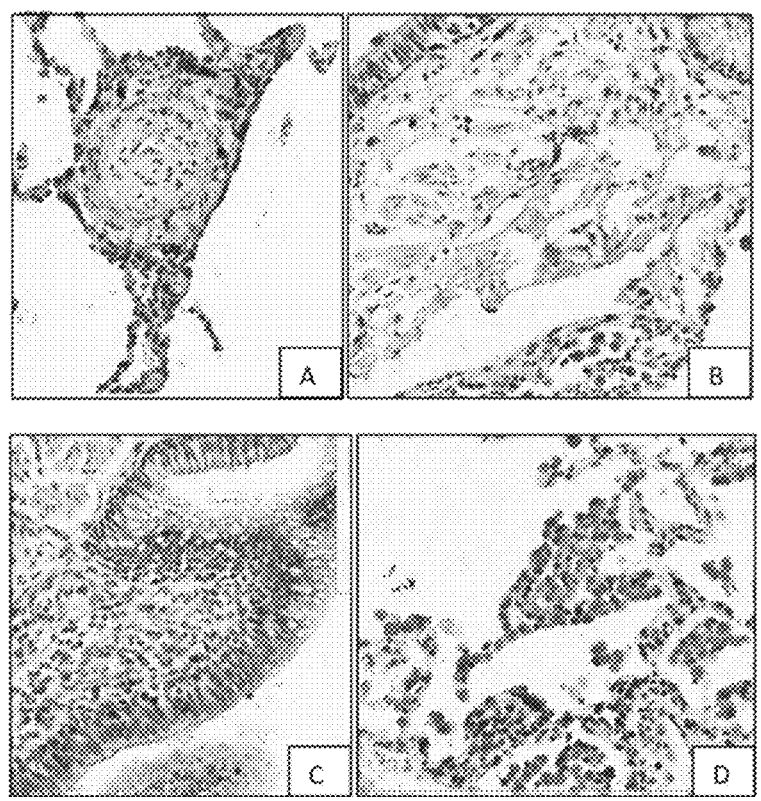
FIG. 3: CCL21 protein expression and localisation by immunohistochemistry in human lung sections from PH patients undergoing lung transplantation.

CCL21 protein was detected in PAH lesions (FIG. 3) from advanced PH patients in areas with subepithelial/epithelial and alveolar macrophages as well as lymphatic vessels. We therefore concluded that CCL21 is expressed at the site of the disease pathology.

REFERENCES

1. Schermuly, R. T., Ghofrani, H. A., Wilkins, M. R. & Grimminger, F. Mechanisms of disease: pulmonary arterial hypertension. *Nature reviews. Cardiology* 8, 443-455 (2011).
2. Galie, N. et al. Guidelines for the diagnosis and treatment of pulmonary hypertension. *The European respiratory journal* 34, 1219-1263 (2009).
3. Dewachter, L. et al. Angiopoietin/Tie2 pathway influences smooth muscle hyperplasia in idiopathic pulmonary hypertension. *American journal of respiratory and critical care medicine* 174, 1025-1033 (2006).
4. Fike, C. D., Slaughter, J. C., Kaplowitz, M. R., Zhang, Y. & Aschner, J. L. Reactive oxygen species from NADPH oxidase contribute to altered pulmonary vascular responses in piglets with chronic hypoxia-induced pulmonary hypertension. *American journal of physiology. Lung cellular and molecular physiology* 295, L881-888 (2008).
5. Price, L. C. et al. Inflammation in pulmonary arterial hypertension. *Chest* 141, 210-221 (2012).
6. Rabinovitch, M. Molecular pathogenesis of pulmonary arterial hypertension. *The Journal of clinical investigation* 122, 4306-4313 (2012).
7. Voelkel, N. F., Gomez-Arroyo, J., Abbate, A., Bogaard, H. J. & Nicolls, M. R. Pathobiology of pulmonary arterial hypertension and right ventricular failure. *The European respiratory journal* 40, 1555-1565 (2012).
8. Kherbeck, N. et al. The role of inflammation and autoimmunity in the pathophysiology of pulmonary arterial hypertension. *Clinical reviews in allergy & immunology* 44, 31-38 (2013).
9. Perros, F. et al. Fractalkine-induced smooth muscle cell proliferation in pulmonary hypertension. *The European respiratory journal* 29, 937-943 (2007).
10. Humbert, M. et al. Increased interleukin-1 and interleukin-6 serum concentrations in severe primary pulmonary hypertension. *American journal of respiratory and critical care medicine* 151, 1628-1631 (1995).
11. Soon, E. et al. Elevated levels of inflammatory cytokines predict survival in idiopathic and familial pulmonary arterial hypertension. *Circulation* 122, 920-927 (2010).
12. Tamby, M. C. et al. Anti-endothelial cell antibodies in idiopathic and systemic sclerosis associated pulmonary arterial hypertension. *Thorax* 60, 765-772 (2005).
13. Terrier, B. et al. Identification of target antigens of antifibroblast antibodies in pulmonary arterial hypertension. *American journal of respiratory and critical care medicine* 177, 1128-1134 (2008).
14. Tuder, R. M., Groves, B., Badesch, D. B. & Voelkel, N. F. Exuberant endothelial cell growth and elements of inflammation are present in plexiform lesions of pulmonary hypertension. *The American journal of pathology* 144, 275-285 (1994).
15. Carragher, D. M., Rangel-Moreno, J. & Randall, T. D. Ectopic lymphoid tissues and local immunity. *Seminars in immunology* 20, 26-42 (2008).
16. Brusselle, G. G., Demoor, T., Bracke, K. R., Brandsma, C. A. & Timens, W. Lymphoid follicles in (very) severe COPD: beneficial or harmful? *The European respiratory journal* 34, 219-230 (2009).
17. Marchal-Somme, J. et al. Cutting edge: nonproliferating mature immune cells form a novel type of organized lymphoid structure in idiopathic pulmonary fibrosis. *J Immunol* 176, 5735-5739 (2006).
18. Sato, M. et al. The role of intrapulmonary de novo lymphoid tissue in obliterative bronchiolitis after lung transplantation. *J Immunol* 182, 7307-7316 (2009).
19. Perros, F. et al. Pulmonary lymphoid neogenesis in idiopathic pulmonary arterial hypertension. *American journal of respiratory and critical care medicine* 185, 311-321 (2012).
20. Aloisi, F. & Pujol-Borrell, R. Lymphoid neogenesis in chronic inflammatory diseases. *Nature reviews. Immunology* 6, 205-217 (2006).
21. Nagaya, N. et al. Plasma brain natriuretic peptide as a prognostic indicator in patients with primary pulmonary hypertension. *Circulation* 102, 865-870 (2000).
22. Giannakoulas, G. et al. Usefulness of natriuretic Peptide levels to predict mortality in adults with congenital heart disease. *The American journal of cardiology* 105, 869-873 (2010).
23. Galie, N. et al. Ambrisentan for the treatment of pulmonary arterial hypertension: results of the ambrisentan in pulmonary arterial hypertension, randomized, double-blind, placebo-controlled, multicenter, efficacy (ARIES) study 1 and 2. *Circulation* 117, 3010-3019 (2008).
24. Mauritz, G. J. et al. Usefulness of serial N-terminal pro-B-type natriuretic peptide measurements for determining prognosis in patients with pulmonary arterial hypertension. *The American journal of cardiology* 108, 1645-1650 (2011).
25. Yoshida, R. et al. Secondary lymphoid-tissue chemokine is a functional ligand for the CC chemokine receptor CCR7. *The Journal of biological chemistry* 273, 7118-7122 (1998).

What is claimed is:

1. A method for treating a patient having pulmonary hypertension, comprising:
   a) assaying a biological sample selected from the group consisting of blood, serum and plasma obtained from the patient for the level of CCL21 expression and/or CCL21 protein;
   b) comparing the amount of CCL21 expression and/or of CCL21 protein to a baseline value that is indicative of the amount of CCL21 expression and/or of CCL21 protein in a subject that does not have pulmonary hypertension; and
   c) administering a therapeutically effective amount of a pulmonary hypertension antagonist if the patient has a statistically significant increased amount of CCL21 expression and/or of CCL21 protein compared to the baseline value, wherein the statistically significant increased amount is 1.5 fold or higher than the baseline value with a p-value of less than or equal to 0.05, as determined using a T-test.

2. The method according to claim 1, wherein the step of assaying comprises assaying the biological sample for a nucleic acid sequence of CCL21 expression.

3. The method according to claim 2, wherein the nucleic acid is CCL21 ribonucleic acid (RNA) or a fragment thereof, or complementary deoxyribonucleic acid (cDNA) or a fragment thereof.

4. The method of claim 1, wherein the step of assaying comprises assaying the biological sample for a CCL21 protein or fragment thereof.

5. The method of claim 1, wherein the step of assaying comprises a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, primer extension assays, oligonucleotide ligase assays, temperature gradient gel electrophoresis (TGGE), denaturing high performance liquid chromatography, high-resolution melting analysis, DNA mismatch-binding protein assays, capillary electrophoresis, Southern Blot, immunoassays, immunohistochemistry, ELISA, flow cytometry, Western blot, HPLC, and mass spectrometry.

6. The method of claim 1, wherein the pulmonary hypertension antagonist is a calcium channel blocker, a phosphodiesterase (PDE) 5 inhibitor, a guanylate cyclase (sGC) stimulator, an endothelin receptor antagonist (ERA), or a prostacyclin agonist.

7. The method of claim 1, wherein the amount of CCL21 expression and/or of CCL21 protein is increased by 50% or higher compared to the baseline value.

8. The method of claim 1, wherein the amount of CCL21 expression and/or of CCL21 protein is increased by 2-fold or higher compared to the baseline value.

9. A method for treating a patient having pulmonary hypertension, comprising:
   a) assaying a biological sample selected from the group consisting of blood, serum and plasma obtained from the patient for the level of CCL21 expression and/or CCL21 protein, wherein a nucleic acid sequence of CCL21 expression or a CCL21 protein or fragment thereof is assayed;
   b) comparing the amount of CCL21 expression and/or of CCL21 protein to a baseline value that is indicative of the amount of CCL21 expression and/or of CCL21 protein in a subject that does not have pulmonary hypertension; and
   c) administering a therapeutically effective amount of a pulmonary hypertension antagonist if the patient has a statistically significant increased amount of CCL21 expression and/or of CCL21 protein, wherein the statistically significant increased amount is 1.5 fold or higher than the baseline value with a p-value of less than or equal to 0.05, as determined using a T-test.

10. The method of claim 9, wherein a nucleic acid sequence of CCL21 expression is assayed, and wherein the nucleic acid is CCL21 ribonucleic acid (RNA) or a fragment thereof, or complementary deoxyribonucleic acid (cDNA) or a fragment thereof.

11. The method of claim 9, wherein a CCL21 protein or fragment thereof is assayed.

12. The method of claim 9, wherein the step of assaying comprises a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, primer extension assays, oligonucleotide ligase assays, temperature gradient gel electrophoresis (TGGE), denaturing high performance liquid chromatography, high-resolution melting analysis, DNA mismatch-binding protein assays, capillary electrophoresis, Southern Blot, immunoassays, immunohistochemistry, ELISA, flow cytometry, Western blot, HPLC, and mass spectrometry.

13. The method of claim 9, wherein the pulmonary hypertension antagonist comprises a calcium channel blocker, a phosphodiesterase (PDE) 5 inhibitor, a guanylate cyclase (sGC) stimulator, an endothelin receptor antagonist (ERA), or a prostacyclin agonist.

14. The method of claim 9, wherein the increased amount is 2-fold or higher compared to the baseline value.

15. A method for treating a patient having pulmonary hypertension, comprising:
   a) assaying a biological sample selected from the group consisting of blood, serum and plasma obtained from the patient for the level of CCL21 expression and/or CCL21 protein;
   b) comparing the amount of CCL21 expression and/or of CCL21 protein to a baseline value that is indicative of the amount of CCL21 expression and/or of CCL21 protein in a subject that does not have pulmonary hypertension; and
   c) administering a therapeutically effective amount of a pulmonary hypertension antagonist if the patient has a statistically significant increased amount of CCL21 expression and/or of CCL21 protein, wherein the statistically significant increased amount is 1.5 fold or higher than the baseline value with a p-value of less than or equal to 0.05, as determined using a T-test, and wherein the pulmonary hypertension antagonist is selected from the group consisting of a calcium channel blocker, a phosphodiesterase (PDE) 5 inhibitor, a guanylate cyclase (sGC) stimulator, an endothelin receptor antagonist (ERA), and a prostacyclin agonist.

16. The method of claim 15, wherein the step of assaying comprises assaying the biological sample for a nucleic acid sequence of CCL21 expression.

17. The method of claim 16, wherein the nucleic acid is CCL21 ribonucleic acid (RNA) or a fragment thereof, or complementary deoxyribonucleic acid (cDNA) or a fragment thereof.

18. The method of claim 15, wherein the step of assaying comprises assaying the biological sample for a CCL21 protein or fragment thereof.

19. The method of claim 15, wherein the step of assaying comprises a technique selected from the group consisting of Northern blot analysis, polymerase chain reaction (PCR), reverse transcription-polymerase chain reaction (RT-PCR), TaqMan-based assays, direct sequencing, dynamic allele-specific hybridization, primer extension assays, oligonucleotide ligase assays, temperature gradient gel electrophoresis (TGGE), denaturing high performance liquid chromatography, high-resolution melting analysis, DNA mismatch-binding protein assays, capillary electrophoresis, Southern Blot, immunoassays, immunohistochemistry, ELISA, flow cytometry, Western blot, HPLC, and mass spectrometry.

20. The method of claim 15, wherein the amount of CCL21 expression and/or of CCL21 protein is increased by 2-fold or higher compared to the baseline value.

* * * * *